Figure 1:
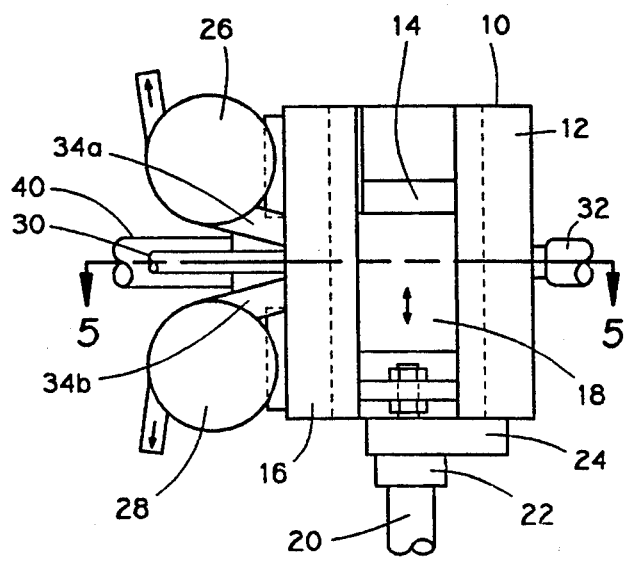
Figure 3:
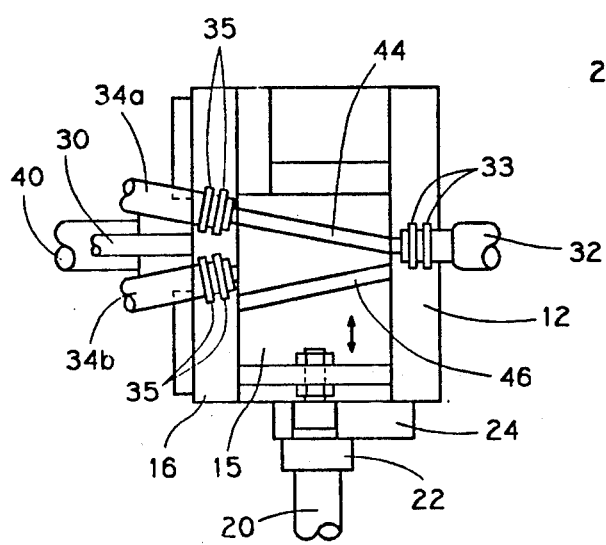
Figure 2:
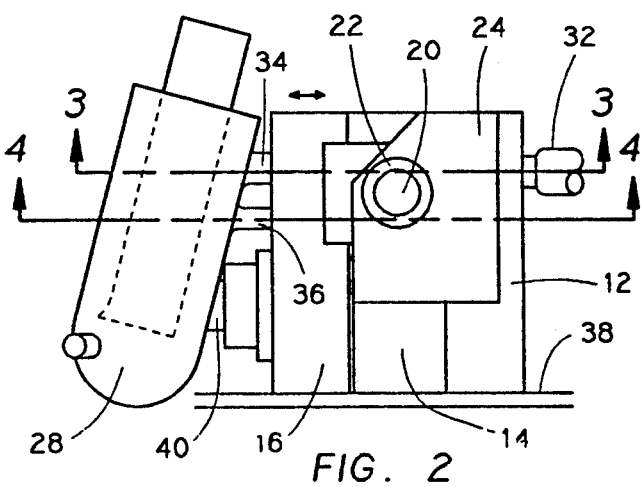
Figure 4:
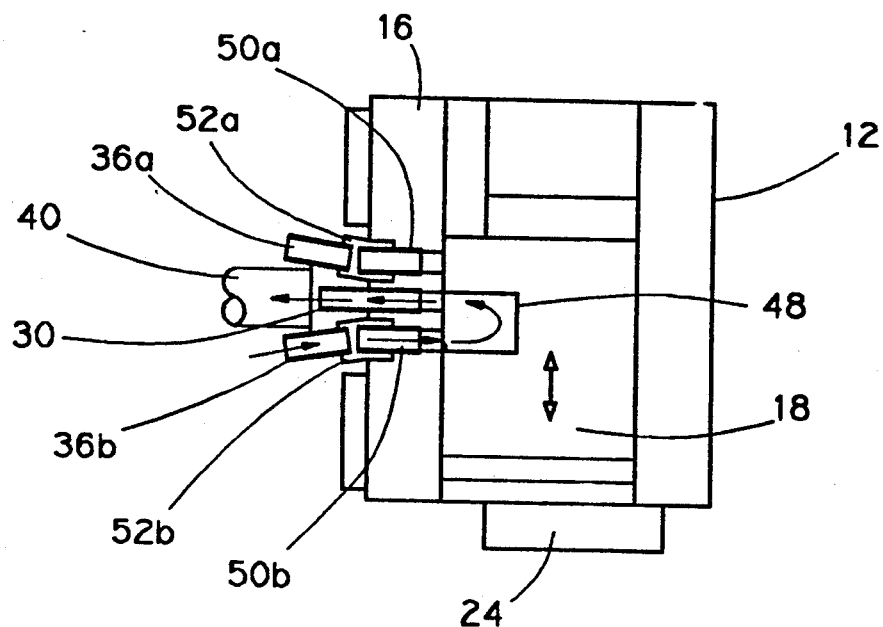

United States Patent [19]

March et al.

[11] Patent Number: 5,313,846
[45] Date of Patent: May 24, 1994

[54] SAMPLE INTRODUCTION VALVE FOR SPECTROMETERS WITH SHUTTLE VALVE

[75] Inventors: David A. March, West Groton; Peter G. Brown, Westford; David A. Hotham, Danvers, all of Mass.

[73] Assignee: Leeman Labs Inc., Lowell, Mass.

[21] Appl. No.: 712,696

[22] Filed: Jun. 10, 1991

[51] Int. Cl.⁵ .................................. G01N 35/00
[52] U.S. Cl. ........................... 73/864.81; 137/625.48; 137/240
[58] Field of Search .................... 137/625.48, 240; 73/864.81, 864.55, 863.33

[56] References Cited

U.S. PATENT DOCUMENTS

| | | | |
|---|---|---|---|
| 4,683,914 | 8/1987 | Brisland | 137/625.48 |
| 4,877,057 | 10/1989 | Christensen | 137/625.48 |
| 4,877,058 | 10/1989 | Stoll | 137/625.48 |
| 4,955,100 | 9/1990 | Bersch | 137/625.48 |

Primary Examiner—Hezron E. Williams
Assistant Examiner—Howard Wisnia
Attorney, Agent, or Firm—John M. Brandt

[57] ABSTRACT

A sample introduction valve for spectrometers for selectively directing sample flow from two or more sources in which a slideably mounted shuttle provides in one position a pass through for one source and a by-pass for the other source and in a second position the opposite result.

2 Claims, 2 Drawing Sheets

SAMPLE INTRODUCTION VALVE FOR SPECTROMETERS WITH SHUTTLE VALVE

BACKGROUND OF THE INVENTION

1. Field of the Invention

The invention resides in the field of sample introduction systems for spectrometry and more particularly relates to valves for presenting samples in aerosol or other form to inductively coupled plasma excitation devices.

2. Description of the Prior Art

Many analytical techniques for the determination of chemical species are limited in the number of samples that can be processed per unit time because of previous sample carry-over effects within the sample introduction system.

The normal procedure for presenting samples to a spectrometer excitation source, inductively-coupled plasma for example, is to first remove traces of the previous sample by pumping or aspirating a blank rinse solution through the sample introduction system. Then after a sufficient passage of time to allow for the previous sample to be effectively washed out, the system begins pumping the new sample and waits for system stabilization, known as uptake time. After the system has stabilized, the analytical data is then collected. In a simultaneous instrument the time required to collect the analytical data can be significantly shorter than the combined washout and uptake time. The present invention involves the use of two or more sample introduction units, such that while data is being collected on the sample resident in one introduction unit the other unit is washing out previous samples or is uptaking a new sample for presentation.

A number of criteria must be considered in the design of the apparatus which comprises the invention. For example, such a system or valve must not allow any undue restrictions or expansions to the aerosol flow which would permit condensation or deposition of the sample aerosol.

It must present to the aerosol the least tortuous path to the excitation source, so as to minimize bends and turns which distort the aerosol flow dynamics which could result in sample condensation or deposition.

The design must minimize the internal volume of the valve to limit as much as possible any previous sample aerosol entrapment.

The system must provide for venting the aerosol that is not traveling to the torch. It is necessary that venting occur during the valve switching so that internal pressures do not increase excessively.

The invention described below meets the above stated criteria and has the features and is constructed according to the following summary.

SUMMARY OF THE INVENTION

The invention may be summarized as a sample introduction valve for spectrometers in which the output of two sample chambers arranged to receive either a sample bearing aerosol or rinse aerosol is directed to either the excitation system of a spectrometer or a by-pass drain. This is accomplished by providing a movable shuttle valve which in one position provides pass through for one sample chamber and by-pass for the other and in a second position the opposite result. Appropriate passages and a by-pass chamber are disposed within the shuttle and the valve is arranged to produce a simultaneous make and break of both aerosol paths. As a result, the number of samples which may be processed in a unit time can be greatly increased with no degradation of accuracy or other adverse effects.

The invention will be more fully understood from the description of the preferred embodiment and drawings which follow.

DESCRIPTION OF THE DRAWINGS

FIG. 1 is an elevation view of the preferred embodiment of the invention;

FIG. 2 is a right side view of the device of FIG. 1;

FIG. 3 is a front cross-sectional view of FIG. 2 along line A—A;

FIG. 4 is a cross-sectional view of FIG. 2 along line B—B; and

FIG. 5 is a cross-sectional view of FIG. 1 along line C—C.

DESCRIPTION OF THE PREFERRED EMBODIMENT

Referring to FIG. 1, an elevation view of the preferred embodiment is illustrated in which valve body 10 consists of fixed top plate 12, center block 14 and vertically movable bottom plate 16. Shuttle 18 is horizontally slideable between plates 12 and 16 and operable by piston 20 in communication with shuttle 18 through bearing blocks 22 and 24. Sample chambers 26 and 28 are mounted in spaced apart relationship upon and below bottom plate 16 on either side of drain pipe 30. Sample outlet pipe 32 extends upwardly from top plate 12.

Referring next to FIG. 2, a right side view of the device of FIG. 1 is shown in which like numbers refer to like parts and additionally illustrated are first and second outlet pipes 34 and 36 for each sample chamber, as will be referred to as 34*a* and *b* and 36*a* and *b* in further description, which pipes communicate with certain passageways in shuttle 18 through bottom plate 16.

Back plate 38 serves as a mount for the entire valve and has top plate 12 and center block 14 attached thereto. Bottom plate 16 is vertically moveable by piston 40 extending through bottom plate 16 for the purpose of forming a gas tight seal between members 10, 16, and 18.

FIG. 3 is a front cross-sectional view along line A—A of FIG. 2 in which transverse passageways 44 and 46 in shuttle 18 communicate with either sample chamber outlet pipes 34*a* or 34*b* through plate 16 and sample outlet pipe 32 depending upon whether the shuttle is in the right as is illustrated, or the left position. O rings 35 provide appropriate seals for pipes 34 and O rings 33 for outlet pipe 32.

As will be seen, the position of the shuttle will allow the aerosol sample emanating from one or the other of the sample chambers to pass to the spectrometer excitation device while blocking the emission from the opposite chamber.

Referring to FIG. 4, a front cross-sectional view along line B—B of FIG. 2 shows the alternative path for spray which is blocked from exiting the valve to the spectrometer. By-pass chamber 48 disposed in shuttle 18 communicates with drain pipe 30 and either sample chamber outlet pipes 36*a* or 36*b* through plate 16 depending upon the right as illustrated or left position of the shuttle. Appropriate pipe fittings 50*a* and 50*b* and flexible tubing sections 52a and 52b facilitate the fluid connections.

Thus it will be clear that by moving the shuttle furthest in one direction, a passageway from one sample chamber to the spectrometer is created while a drain path for washout of prior sample material is simultaneously created for the opposite chamber. Moving the shuttle furthest in the opposite direction reverses the pathway orientation resulting in the ability to carry out the procedures of sample presentation and system cleansing at the same time.

Figure 5:
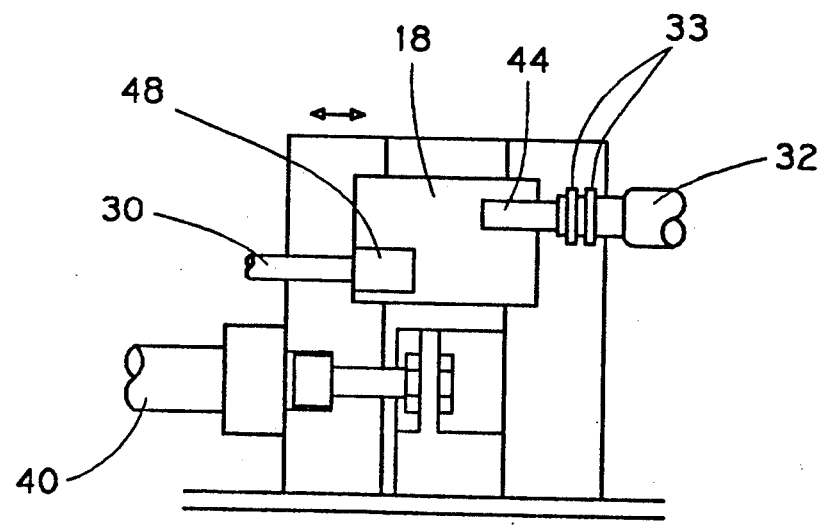

Referring next to FIG. 5, a cross-sectional side view along line C—C illustrates the feature of the invention which provides for a gas tight seal between the components by moving bottom plate upwardly and releasing the same by retraction.

Having fully described the preferred embodiment certain variations will become apparent to those skilled in the art. Accordingly, the invention is defined by the following claims.

What is claimed is:

1. A sample introduction valve for spectrometers comprising in combination:
   a. a valve body;
   b. a shuttle slideably mounted in said body said shuttle having a by-pass chamber and a pair of spaced apart transverse passageways disposed therein;
   c. a first sample chamber for receiving an aerosol spray;
   d. a second sample chamber for receiving an aerosol spray, each of said chambers having a first outlet port aligned with one of said transverse passageways and a second outlet port aligned with said by-pass chamber;
   e. a drain pipe disposed in said valve body aligned with said by-pass chamber; and
   f. a sample outlet pipe connected to said spectrometer disposed in said valve body aligned with said transverse passageways when said shuttle is in a first position a fluid connection from said first sample chamber to said outlet is created and a fluid connection from said second sample chamber to said by-pass chamber to said drain is also created; and when said shuttle is in a second position, a fluid connection from said second sample chamber to said outlet is created and a fluid connection from said first sample chamber to said by-pass chamber to said drain is also created.

2. The apparatus of claim 1 wherein said valve body comprises a top plate and a bottom plate, wherein said shuttle is mounted between said plates, and wherein one of said plates is moveable with respect to the other whereby said shuttle may be frictionally held in position by such movement.

* * * * *